(12) United States Patent
Morrison et al.

(10) Patent No.: US 7,153,930 B1
(45) Date of Patent: Dec. 26, 2006

(54) PEPTIDE TRANSPORT

(76) Inventors: James Duncan Morrison, West Medical Building University of Glasgow, University Avenue, Glasgow G12 8QQ (GB); Michael Leslie Lucas, West Medical Building University of Glasgow, University Avenue, Glasgow G12 8QQ (GB); Sarah Wheeler, West Medical Building University of Glasgow, University Avenue, Glasgow G12 8QQ (GB)

( * ) Notice: Subject to any disclaimer, the term of this patent is extended or adjusted under 35 U.S.C. 154(b) by 110 days.

(21) Appl. No.: 10/088,807

(22) PCT Filed: Jul. 28, 2000

(86) PCT No.: PCT/GB00/02903

§ 371 (c)(1), (2), (4) Date: Jul. 29, 2002

(87) PCT Pub. No.: WO01/09163

PCT Pub. Date: Feb. 8, 2001

(30) Foreign Application Priority Data

Jul. 30, 1999 (GB) ................................ 9917793.3

(51) Int. Cl.
*A61K 38/00* (2006.01)
(52) U.S. Cl. .................................................... 530/303
(58) Field of Classification Search ................ 530/300, 530/303; 514/4, 15; 424/455, 19
See application file for complete search history.

(56) References Cited

U.S. PATENT DOCUMENTS

| | | | | |
|---|---|---|---|---|
| 4,579,730 A | * | 4/1986 | Kidron et al. ................. 424/19 |
| 4,994,439 A | * | 2/1991 | Longenecker et al. ......... 514/3 |
| 5,053,389 A | * | 10/1991 | Balschmidt et al. ........... 514/4 |
| 5,204,108 A | | 4/1993 | Illum .......................... 424/434 |
| 5,428,182 A | | 6/1995 | Enhsen et al. ............... 552/509 |
| 5,446,026 A | * | 8/1995 | Ruff et al. ..................... 514/15 |
| 5,641,497 A | | 6/1997 | Bevins et al. ................ 424/405 |
| 5,641,767 A | | 6/1997 | Wess et al. .................... 514/172 |
| 5,646,272 A | | 7/1997 | Kramer et al. ................... 540/5 |
| 5,668,126 A | | 9/1997 | Kramer et al. ............... 514/176 |
| 5,837,841 A | | 11/1998 | Bandman et al. .......... 536/23.5 |
| 5,861,494 A | | 1/1999 | Soppet et al. .............. 536/23.1 |
| 5,866,536 A | | 2/1999 | Leone-Bay et al. ............ 514/2 |
| 5,929,033 A | | 7/1999 | Tang et al. .................... 514/12 |
| 6,080,722 A | | 6/2000 | Soppet et al. ................. 514/12 |
| 6,171,816 B1 | | 1/2001 | Yu et al. ..................... 435/69.1 |
| 6,245,753 B1 | * | 6/2001 | Byun et al. .................... 514/56 |
| 6,251,428 B1 | * | 6/2001 | Yoo ............................ 424/455 |

FOREIGN PATENT DOCUMENTS

| | | |
|---|---|---|
| EP | 0689052 A2 * | 12/1995 |
| WO | WO 96/06635 | 3/1996 |
| WO | WO 98/00169 | 1/1998 |
| WO | WO 98/01159 | 1/1998 |
| WO | WO 01/22920 A2 | 4/2001 |

OTHER PUBLICATIONS

Swaan, P.R., et al., "Enhanced transepithelial transport of peptides by conjugation to cholic acid," Bioconjugate Chem., 8: 520-525 (1997).*
Kramer et al. Liver-specific drug targeting by coupling to bile acids. J Biol Chem. Sep. 15, 1992;267(26):18598-604.*
Manning et al. Stability of protein pharmeceuticals. Pharm. Res. vol. 6 (11), 1989: 903-17.*
Rudikoff et al. Single amino acid substitution altering antigen-binding specificity. Immunology. vol. 79, Mar. 1982: 1979-83.*
Kramer, W., et al., "Intestinal Absorption of Peptides by Coupling to Bile Acids," *The Journal of Biological Sciences*, 269(14): 10621-10627 (1994).
Stephan, Z. F., et al., "Reduction of Cardiovascular and Thyroxine-Suppressing Activities of L-$T_3$ by Liver Targeting with Cholic Acid," *Biochemical Pharmacology*, 43(9): 1969-1974 (1992).
Swaan, P. R., et al., "Enhanced Transepithelial Transport of Peptides by Conjugation to Cholic Acid," *Bioconjugate Chem.*, 8: 520-525 (1997).
Wickboldt, A., et al., "Drug-Targeting by Bile Acids: Uptake and Secretion of Bile Acid-Peptide Conjugates to the Liver," *Arch. Pharmacol.*, 357(4): Suppl. R8 No. 20 (1998). (Abstract).
Porte, et al., Neoplastic Progression of Human Colorectal Cancer is Associated with Overexpression of the Stromelysin-3 and BM-40/SPARC, Genes, Int. J. Cancer, 1995, 64, 70-75.
Thompson, et al., hAG-2, Human Homologue of the *Xenopus laevis* Cement Gland Gene XAG02, Is Coexpressed with Estrogen Receptor in Breast Cancer Cell Lines, Biochemical and Biophysical Research Communications, 1996, 251, 111-116.
Hartupee, et al., Isolation and characterization of cDNA encoding a novel member of the human regenerating protein family: Reg. IV[1], Biochimica et Biophysica Acta, 2001, 1518 287-293.

(Continued)

*Primary Examiner*—Christopher R. Tate
*Assistant Examiner*—Maury Audet
(74) *Attorney, Agent, or Firm*—Fish & Neave IP Group Ropes & Gray LLP

(57) ABSTRACT

The present invention relates to improving and/or increasing the bioavailability of a biologically active substance, such as a peptide. In particular, the present invention relates to the conjugation of the biologically active substance to a bile acid. The conjugated biologically active substance is suitable particularly for oral or parental administration.

18 Claims, No Drawings

OTHER PUBLICATIONS

Wheeler, S., et al., "Absorption of biologically active peptide hormones from the small intestine of rat," Acta Physiol Scand 2002, 176, 203-213.

McHarg, S., et al., "Absorption of the cholic acid-conjugated peptide hormone cholylsecretin from the rat ileum in vivo," Acta Physiol Scand 2004, 181, 1-12.

* cited by examiner

PEPTIDE TRANSPORT

RELATED APPLICATIONS

This application claims priority under 35 U.S.C. § 371 from PCT Application No. PCT/GB00/02903, filed in English on Jul. 28, 2000, which claims the benefit of Great Britain Application Serial No. 9917793.3 filed on Jul. 30, 1999, the disclosures of which are incorporated by reference herein in their entireties.

The present invention relates to improving and/or increasing the bioavailability of a biologically active substance, such as a peptide. In particular the present invention relates to the conjugation of the biologically active substance to a bile acid. The conjugated biologically active substance is suitable particularly for oral or parenteral administration.

Of all the routes of administration utilised by medicine, oral ingestion is commonly believed to be the most preferred. Such a route of administration, which may be by means of syrup, elixir, tablets, capsules, granules, powders or any other convenient formulation, is generally simple and straightforward and is frequently the least inconvenient or unpleasant route of administration from the patients' point of view.

However, most biologically active materials are very poorly absorbed when administered orally. This is a result of the acidic and hydrolytic environments of the stomach and small intestine, which are hostile to many materials, including proteins, and the intestinal epithelium which acts as a potential barrier to the passage of biologically active materials.

It is possible to provide enteric coated formulations which are protected from the acid environment of the stomach and which allow the biologically active material to survive its passage through the stomach and to be taken up by the body in the small intestine. However, relatively large molecules such as peptides and proteins are poorly absorbed by the small intestine.

As a result, proteinaceous medicaments, such as insulin which is used to treat diabetes mellitus, have to be taken parenterally, often by subcutaneous, intramuscular or intravenous injection, with all the inconvenience, discomfort and difficulties of patient compliance that this entails.

Besides diabetes mellitus, there are numerous other conditions which require treatment by administration of a proteinaceous compound or another macromolecule. Osteoporosis is a further example of a condition which can be treated with a protein, in this case calcitonin. Another example is dwarfism which is treated with the administration of protein growth hormones.

It has been found that when pharmaceutically-active compounds are administered together with certain bile acids together with a buffer, the bioavailability is increased (WO 96/06635). Where the biologically active material is associated with but not conjugated to a bile acid, it is believed that the bile acid improves absorption of biologically active materials as a result of their action on the cell membranes of epithelial cells.

U.S. Pat. No. 5,641,767 discloses the use of covalently modified bile acids which are suitable for oral administration. However, the modified bile acids themselves are employed as active pharmaceutical agents.

U.S. Pat. No. 5,646,272 describes a bile acid derivative having an active compound bound directly to the bile acid ring system via a bonding member. The bile acid has been shown to assist in the uptake of the active material.

Kramer et al (J. Biol. Chem (1994) 269 pp 10621–10627) describes how the attachment of a peptide to the C3 position of the bile acid increases uptake of the peptide.

Additionally Stephan et al (Biochem. Pharmacol. (1992), 43 pp 1969–1974) describes how the conjugation of thyroid hormone (L-$T_3$) to the carboxy group of cholic acid assists the uptake of the hormone. However, this document teaches the use of conjugated bile acid to target the hormone predominantly to the liver in order to minimise access to non-hepatic cells and thus reduce undesirable side effects.

The present invention is based on the unexpected discovery that conjugation of a pharmaceutically active substance to a bile acid via the carboxylic acid group of the bile acid results in improved uptake of the active substance into the blood stream when administered orally.

Moreover, it has also been observed that such conjugated material may be administered parenterally at much lower doses than the unconjugated form of the biologically active substance.

In a first aspect the present invention provides an amide of a bile acid/salt, wherein the group bound to the bile acid/salt by the amide bond is a peptide of formula (I):

$$-X-Y \qquad (I)$$

wherein
- X is at least one polypeptide chain of at least 4 amino acids in length which may be linear, branched or comprise two or more cross-linked polypeptide chains; and
- Y is OH, $NH_2$, or a $C_1$–$C_6$ ester group bonded to the terminal carboxy of the polypeptide chain.

In a further aspect the present invention provides an amide of a bile acid/salt of formula (II):

wherein
- $R^1$ to $R^5$ are independently selected from OH, H or $C_{1-6}$ alkyl; and
- A is $-R^6-CO-X-Y$ wherein
- $R^6$ is $C_2$ to $C_6$ branched or linear alkylene;
- X is at least one polypeptide chain of at least 4 amino acids in length which may be linear, branched or comprise two or more cross-linked polypeptide chains; and
- Y is is OH, $NH_2$, or a $C_1$–$C_6$ ester group bonded to the terminal carboxy of the polypeptide chain.

In the present invention it should be understood that the terms bile salt and bile acid are used interchangeably since the pH of the surrounding environment will determine whether the salt or its acid is present.

The peptide is conjugated to the bile salt by means of an amide bond. This amide bond may be formed by covalently bonding to the carboxy group of the bile salt either an a amine or α-imine group or any other amine or imine group belonging to the side chains of the amino acids of the peptide. Such amino and imino acids having an amine group on a side chain include proline, tryptophan, lysine, arginine, histidine, asparagine, glutamine, or any other suitable synthetic or natural amino or imino acid. Therefore, it will be appreciated that more than one bile salt may be conjugated to the one polypeptide chain or protein which may result in a greater uptake of conjugated bile salt-peptide.

Furthermore, these amino or imino groups may be either located at the beginning of the peptide chain or may be located in the interior of the polypeptide chain.

Typically the peptide is at least 4 amino acids long. More typically, the peptide is from 4 to 600 amino acids long, such as 4 to 200 amino acids long. The term "peptide" therefore encompasses polypeptides and proteins. Furthermore, peptides modified by, for example, glycosylation, can also be utilised in the present invention, as can a protein comprising two or more polypeptide chains each of length of 4 to 600 amino acids long cross-linked by, for example, disulphide bonds, for example, insulin and immunoglobulins.

Bile salts may be mono-, di- or tri-hydroxylated and may contain a 3α-hydroxyl group. The other hydroxyl groups, most commonly found at $C_7$ or $C_{12}$, may be positioned either above (β) or below (α) the plane of the molecule.

Within the class of compounds described as bile salts are included amphiphilic polyhydric sterols bearing carboxyl groups as part of the primary side chain. The most common examples of these in mammals result from cholesterol metabolism and are found in the bile and, in derivatised form, throughout the small and large intestine.

In the context of this specification, the terms "bile salt" or bile acids" may also apply to synthetic analogues of naturally occurring bile salts/acids which display similar biological effects, or to microbially derived molecules and their derivatives.

The bile salt (or salts) may be either underivatised or derivatised. The term "underivatised" refers to a bile salt in which the primary side chain has a single carboxyl group at the terminal position and is unsubstituted.

Thus, in the present invention, examples of suitable underivatised bile salts include cholate, deoxycholate, chenodeoxycholate and ursodeoxycholate, with cholate being particularly preferred.

It is to be understood that the present invention may also utilise bile salts that have been derivatised. For example a derivatised bile salt may be one in which the primary side chain has a carboxyl group which is substituted. Often the substituent will be an amino acid derivative which is linked via its nitrogen atom to the carboxyl group of the bile salt. Derivatised bile salts which may be employed include taurocholate, taurodeoxycholate, tauroursodeoxycholate, taurochenodeoxycholate, glycholate, glycodeoxycholate, glycoursodeoxycholate, glycochenodeoxycholate, taurolithocholate and glycolithocholate.

It is to be understood that derivatised bile salts may be employed in the present invention by either underivatising and conjugating the peptide to the bile salt or by conjugating the peptide to the amino acid derivative on the derivatised bile salt.

Examples of particular polypeptides or proteins which may be employed in the present invention include insulin, secretin, gastrin, gastrin releasing peptide, glucagon, cholecystokinin (CCK) gastric inhibitory peptide (also known as glucose insulinotropic peptide (GIP)), parathyroid hormone, thyrotropin-releasing hormone, gonadotropinreleasing hormone (also known as lutenizing hormone-releasing hormone (LHRH)), corticotropin-releasing hormone, somatostatin, adrencorticotropic hormone (ACTH), renin, angiotensin I, angiotensin II, atrial natriuretic hormone (ANH), somatomedins such as insulin-like growth factors IGF1 and IGF2, calcitonin, haemoglobin, cytochrome C, horseradish peroxidase, aprotinin, mushroom tyrosinase, erythropoietin, somatotropin (growth hormone), growth hormone releasing hormone, galanin, urokinase, Factor IX (also known as Christmas factor), tissue plasminogen activator, antibodies such as IgG, IgM, IgA, IgD and IgE, superoxide dismutase, catalase, peroxidase, ferritin, interferon, Factor VIII, soy bean trypsin inhibitor, GLP1, other blood coagulation factors, somatostatin, antidiuretic hormone (ADH), oxytocin, polysaccharides, hirudin, and glycoproteins, such as follicle stimulating hormone (FSH), lutenizing hormone (LH), inhibin, chorionic gonadotropin (CGT) and thyroid stimulating hormone (TSH), and analogues and fragments of all of these and all of which can be from any suitable source.

Furthermore, mixtures of one or more of these or any proteins may be employed in the present invention.

Whilst it is possible for the active conjugated peptide to be administered alone, it is preferable to present the active conjugated peptide in a pharmaceutical formulation. Thus in a further aspect, the present invention provides a pharmaceutical formulation, comprising a conjugated peptide according to the present invention and a pharmaceutically acceptable carrier.

Formulations of the present invention, for medical use, comprise a conjugated peptide together with one or more pharmaceutically acceptable carriers and optionally other therapeutic ingredients. The carrier(s) should be pharmaceutically acceptable in the sense of being compatible with the other ingredients of the formulation and substantially non-deleterious to the recipient thereof.

Preferably, the pharmaceutical formulation is formulated to be administered orally.

Typically the pharmaceutical formulation may be protected, such as by encapsulation, to prevent degradation in the stomach in order for the conjugated peptide to reach the small intestine substantially intact for uptake by the ileum.

In addition, there is provided as a further, or alternative, aspect of the invention, a conjugated peptide according to the present invention, or a physiologically functional derivative thereof, for use in therapy.

The amount of conjugated peptide required to be effective will, of course, vary and is ultimately at the discretion of the medical or veterinary practitioner. The factors to be considered include the condition being treated, the route of administration, and nature of the formulation, the mammal's body weight, surface area, age and general condition and the particular compound to be administered. A suitable effective dose of compounds of the invention generally lies in the range of about 0.01 to about 120 mg/kg bodyweight, e.g. 0.1 to about 120 mg/kg body weight, preferably in the range of about 0.1 to 50 mg/kg, for example 0.5 to 50 mg/kg. The total daily dose may be given as a single dose, multiple doses, e.g. two to six times applications per day. For example, for a 75 kg mammal (e.g. a human) the dose range would be about 8 to 9000 mg per day, and a typical dose could be about 50 mg per day. If discrete multiple doses are indicated treatment might typically be 15 mg of a compound of Formula (I) given up to 4 times per day.

There is also provided a method for the preparation of a pharmaceutical formulation comprising bringing into association a conjugated peptide of the present invention, and a pharmaceutically acceptable carrier therefor.

Formulations of the present invention suitable for oral administration may be presented as discrete units such as capsules, sachets, tablets, lozenges, comprising the active ingredient in a flavoured base, usually sucrose and acacia or tragacanth; or pastilles comprising the active ingredient in an inert base such as gelatin and glycerin, or sucrose and acacia. Each formulation generally contains a predetermined amount of the active compound; as a powder or granules; or a solution or suspension in an aqueous or non-aqueous liquid such as a syrup, an elixir, an emulsion or draught and the like.

A tablet may be made by compression or moulding, optionally with one or more accessory ingredients. Compressed tablets may be prepared by compressing in a suitable machine the active compound in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide the desired release profile.

A syrup may be made by adding the active compound to a concentrated, aqueous solution of a sugar, for example sucrose, to which may also be added any necessary ingredients. Such accessory ingredient(s) may include flavourings, an agent to retard crystallization of the sugar or an agent to increase the solubility of any other ingredients, such as a polyhydric alcohol, for example glycerol or sorbitol.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

In a further aspect the present invention provides the use of a conjugated peptide of the present invention in the manufacture of a medicament in a form suitable for oral administration.

In yet a further aspect, the present invention provides the use of a conjugated peptide of the present invention in association with unconjugated peptide.

As mentioned above it has also been found that conjugation of a biologically active material such as a peptide to a bile salt or acid allows lower doses of the biologically active material to be administered parenterally. That is, the pharmacokinetics and/or bioavailability of a biologically active material are improved when a bile salt or acid conjugated biologically active material is added parenterally.

Thus, in a further aspect, the present invention provides use of a compound according to Formula (III):

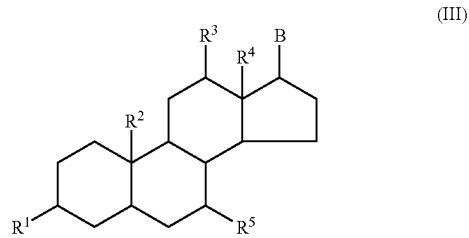

(III)

wherein
$R^1$ to $R^5$ are independently selected from OH, H or $C_{1-6}$ alkyl; and
B is —$R^6$—CO—Z wherein
$R^6$ is $C_2$ to C6 branched or linear alkylene; and
Z is a pharmaceutically active agent; in the manufacture of a medicament suitable for parenteral administration.

The term "pharmaceutically active agent" used herein is defined as any substance, natural or synthetic, which has a physiological action on a living body.

Typically, Z may be bound to the bile acid/salt by an amide linkage.

Examples of suitable pharmaceutical agents include polypeptides and glycoproteins, as described herein above as well as polysaccharides, such as heparin, oligonucleotides/polynucleotides and analogues which may be useful in interfering with replication of nucleic acids in virally infected or cancerous cells and for correcting other forms of inappropriate cell proliferation, or as a means of delivery of a sequence of nucleotides for the purpose of enhancing the synthesis of natural compounds otherwise deficit in the body to compensate for that deficiency. Other suitable pharmaceutical agents include anaesthetics such as thiopentone, anxiolytics such as diazepam, hypnotics such as temazepam, neuroleptics such as chlorpromazine, anti-depressants such as amitriptyline, anti-epileptics such as clonazepam, anti-Parkinsonian drugs such as apomorphine, opioid analgesics such as endorphins, dynorphins and enkephalins, neuropeptide transmitters such as vasoactive intestinal polypeptide (VIP), neuropeptide transmitter antagonists such as [$Lys^1$, $Pro^{2,5}$, $Arg^{3,4}$, $Tyr^6$]-VIP, muscarinic agonists such as pilocarpine, anticholinesterases such as neostigmine, muscarinic antagonists such as cyclopentolate, nicotinic antagonists such as suxamethonium, direct sympathomimetics such as oxymetazdine and salbutamol, indirect sympathomimetics such as tyramine, adrenergic blocking drugs such as guanethidine, adrenoceptor antagonists such as prazosin, vasodilators such as captopril, anti-angina drugs such as isosorbide, cardiotonic drugs such as digoxin, anti-dysrhythmic drugs such as atenolol, anti-coagulants such as streptokinase and alteplase, plasma lipid lowering drugs such as gemfibrozil, anti-anaemia drugs such as iron sorbitol, anti-inflammatory drugs such as phenylbutazone, diuretics such as frusemide, histamine antagonists such as cetirizine, anti-peptic ulcer drugs such as omeprazole or ranitidine, anti-gut motility disorder drugs such as loperamide, chemotherapy drugs such as nalidixic acid, ryfamicin, tetracycline and tamoxifen, anti-bacterial drugs such as gramicidin A, penicillins and sulphonamide, anti-viral drugs such as acyclovir, antifungal drugs such as fluconazole and anti-parasite drugs such as chloroquine, amongst others.

EXAMPLE 1

Physiological Experiments In Vivo

Experiments were carried out on male Wistar rats of 250–350 g, which had been starved overnight, and which were anaesthetized with an I.P. injection of Sagatal (pentobarbitone sodium, obtainable from Rhône Mérieux, Harlow Essex, UK) of dosage appropriate to the body weight. The criterion for anaesthesia was abolition of the hind limb flexor withdrawal reflex. The following surgical procedures were then carried out: tracheostomy to allow artificial ventilation if required, cannulation of the carotid artery to monitor blood pressure, cannulation of the external jugular vein to allow for the slow bolus infusion of drugs, intubation of the stomach at the pyloro-duodenal junction after ligation of the oesophagus to measure gastric acid secretion, cannulation of the terminal ileum and/or of the proximal jejunum distal to the ligament of Treitz for infusion of peptide hormones.

Gastric acid secretion was measured by the following method. 1.0 ml of glycine/mannitol buffer (1 part glycine (0.3M) and 4 parts D-mannitol (0.3M) adjusted to pH 6.5) was instilled into the stomach and left for 15 min when withdrawal was made. The HCl secreted was determined by back titration with 10 mM NaOH to pH 6.5.

The following test substances were used: Gastrin tetrapeptide (G4) (Trp-Met-Asp-Phe amide (Sigma Chemical Co. T-6515), cholate-Trp-Met-Asp-Phe amide conjugate (G4–CA), gastrin decapeptide (G10) (H-Glu-Glu-Glu-Ala-Tyr-GlyTrp-Met-Asp-Phe-amide), cholate-Glu-Glu-Glu-Ala-Tyr-Gly-Trp-Met-Asp-Phe-amide (G10-CA), 34 mergastrin (pGlu-Leu-Gly-Pro-Gln-Gly-Pro-Gln-His-Phe-Ile-Ala-Asp-Leu-Ser-Lys-Lys-Gln-Arg-Pro-Pro-Met-Glu-Glu-Glu-Glu-Glu-Ala-Tyr-GlyTrp-Met-Asp-Phe-NH$_2$) and cholate-Glu-Leu-Gly-Pro-Gln-Gly-Pro-Gln-His-Phe-Ile-Ala-Asp-Leu-Ser-Lys-Lys-Gln-Arg-Pro-Pro-Met-Glu-Glu-Glu-Glu-Glu-Ala-Tyr-Gly-Trp-Met-Asp-Phe-NH$_2$ (G34-CA) the latter five being synthesised de novo using Pioneer Peptide Synthesis System, PerSeptive Biosystems. For cholate-conjugated peptides, the final stage involved coupling of the terminal carboxyl group of cholic acid with the amine group of last amino acid in the peptide sequence. The method which is described in the Pioneer Peptide Synthesis User's Guide will be known to those skilled in the art of peptide synthesis.

The composition and purity of the sample was confirmed with mass spectrometry and HPLC.

Results

The data are expressed as the mean±S.D. μmol HCl secreted by the stomach over the stated time period in response to the experimental procedure.

Experiments with Gastrin Tetrapeptide (G4)

It was first confirmed that biologically active G4 was not absorbed across the wall of the small intestine as illustrated by a typical experiment in FIG. 2.

In 6 experiments, ileal infusion of a large dose of G4 (2500 μg kg$^{-1}$ in 1.0 ml isotonic saline) actually resulted in a fall in the mean gastric acid level of 0.23±0.21 mol hr$^{-1}$ which was significant (P=0.043). In response to intravenous injections at the start and end of the experiment, gastric acid secretion increased significantly with respect to baseline by 0.42±0.10 μmol 15 min$^1$ (P=0.001) for the first injection and by 0.50±0.14 μmol 15 min$^1$ (P=0.001) in response to the second injection: these confirmed the responsiveness and continued viability of the preparation. Thus, it was demonstrated that G4 was not absorbed across the wall of the ileum. In another series of experiments, this lack of absorption of G4 was also confirmed for the upper jejunum.

The key experiment was to test whether G4-CA was absorbed from the small intestine: in this case, the relatively low dose of 600 μg kg$^{-1}$ G4-CA was injected intra-ileally. However, first, it was necessary to confirm that G4-CA had normal biological activity when injected intravenously. The first intravenous injection of G4-CA (15 μg kg$^{-1}$) caused a significant mean peak increase above baseline in total acidity of 0.64±0.26 μmol 15 min$^{-1}$ (P=0.017), while the second I.V. injection also caused a significant increase of 0.72±0.26 μmol 15 min$^{-1}$ (P=0.003).

In a total of 17 rats, ileal administration of G4-CA (600 μg kg$^{-1}$) resulted in a significant mean increase in gastric acid secretion of 1.84±1.49 μmol (P=0.045) over the 3 hr collection period, as illustrated by FIG. 3.

When a solution of tetragastrin and glycocholic acid was added (used in place of cholic acid which by itself is essentially insoluble) so that the ratio of peptide: bile acid in solution was the same as that of the ileally-infused conjugate (approx. 3:2 ratio by weight), the mean response in 5 rats was to cause a drop in mean gastric acid secretion of 0.12±0.22 μmol 180 min$^{-1}$, which was not significantly different from baseline levels (P=0.28).

When the G4-CA was infused into the jejunum, no increase in gastric acid secretion occurred. Furthermore, when this jejunal infusion was then followed after 3 hr by ileal infusion of G4-CA, gastric acid secretion was strongly stimulated.

In 5 rats, infusion of G4-CA (600 μg kg$^{-1}$ in 11.0 ml) into the jejunum caused a significant mean reduction in gastric acid levels of 0.70±0.41 μmol 180 min$^{-1}$ (P=0.018). By contrast, when G4-CA (600 μg kg$^{-1}$) was subsequently injected intra-ileally (third arrow), the gastric acid levels were significantly increased by 1.63±0.31 μmol (P=0.001).

These results demonstrate the absorption of G4-CA with biological activity preserved. The effect required active conjugation of cholic acid to the tetrapeptide since an effect was not present with either tetragastrin alone or with the separate components of the conjugate. Furthermore, the absorption did not occur from the jejunum but was specific to the ileum: this indicates a requirement for bile salt facilitated transport.

Experiments with Gastrin Decapeptide (G10)

The action of G10 on gastric acid secretion when injected I.V. in the same molar dose as G4 (36 μg kg$^{-1}$) in 5 rats was to cause a significant stimulation of the peak gastric acid secretion by 1.28±0.93 μmol (P=0.036) in response to the initial injection and by 1.45±1.15 μmol (P=0.048) in response to the second injection at the end of the experiment. Infusion of a large dose of G10 (6600 μg kg$^{-1}$ in 1.0 ml) into the ileum did not significantly affect gastric acid secretion (−1.22±1.93 μmol 180 min$^{-1}$, P=0.23).

By contrast, G10-CA proved to cause responses showing several differences from G10. In 5 rats the following results were obtained. First, G10-CA I.V. was biologically much more active than G10. Even after reduction of the dose to 3.3 μg kg$^{-1}$ a marked stimulation of gastric acid secretion resulted as shown by significant increases in the mean peak responses: 5.69±1.46 μmol (P=0.001) in response to the first injection and 7.32±2.69 μmol (P=0.004) in response to the second injection. This implies that conjugation of G10 to cholate improves bioavailability and activity of G10 when administered intravenously.

When G10-CA was infused intra-ileally on the same molar basis as G4-CA (1000 μg kg$^{-1}$ in 1.0 ml), there was considerable stimulation of gastric acid secretion with a mean increase of 21.45±14.42 μmol 180 min$^{-1}$ (P=0.029). This confirms that longer peptides are transportable across the wall of the ileum.

Experiments with 34 Mer-Gastrin (G34)

In 5 rats, the action of G34 on gastric acid secretion when injected I.V. with a near threshold dose (10 ng kg$^{-1}$) was to cause a significant stimulation of the peak gastric acid secretion by 0.14±0.034 μmol (P=0.0008) in response to the initial injection and 0.23±0.051 μmol (P=0.0005) in response to the second injection at the end of the experiment. Infusion of G34 at the high dose of 10.5 mg kg$^{-1}$ in 1.0 ml into the ileum did not cause a significant change in mean gastric acid secretion (0.202±0.262 µmol 180 min$^{-1}$, P=0.16).

G34-CA, injected intravenously on an equimolar basis (14 ng kg$^{-1}$), caused significantly greater responses than G34 (P<0.0036). In response to the first I.V. injection, the mean peak response was 0.254±0.023 mmol (P=0.0001) and in response to the second I.V. injection was 0.400±0.047 µmol (P=0.0001). When G34-CA was infused intra-ileally (2700 µg kg$^{-1}$ in 1.0 ml), stimulation of gastric acid secretion occurred with a mean increase of 1.742±0.277 µmol 180 min$^{-1}$ (P=0.0001). This confirms that a molecule as large as 34mer gastrin is transportable across the wall of the small intestine.

Additional Observation

In the prior art, the absorption of peptide hormones or polysaccharides has been described by the mixing of the peptide hormone or polysaccharide with other transport enhancing substances, including bile salts (WO 96/06635 and U.S. Pat. No. 5,866,536). Such a facilitatory action has also been observed with the cholate conjugated derivatives of the present invention. After introduction of the cholate conjugated form of gastrin (G4-CA, G10-CA, G34-CA) into the ileum, absorption of the conjugated gastrin across the ileal wall into the circulation occurred. When this was followed by ileal instillation of the unconjugated form of gastrin (G4, G10, G34, respectively), absorption of the unconjugated gastrin occurred with a resultant stimulation of gastric acid secretion, whereas injection of the unconjugated gastrin without prior injection of the respective conjugate was without effect on gastric acid secretion. In 4 rats, intraileal infusion of G34 subsequent to intraileal infusion of G34-CA caused a mean increase in gastric acid secretion of 5.68±1.38 µmol 180 min$^{-1}$ (P=0.004).

What is claimed is:

1. A method of administering a pharmaceutical composition, comprising
   i) providing a pharmaceutical composition comprising an amide of a bile acid/salt of formula (II)

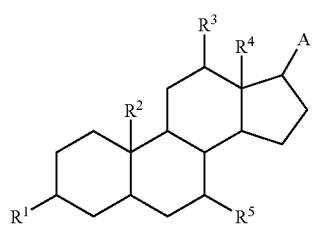

(II)

wherein
   $R^1$ to $R^5$ are independently selected from OH, H or $C_{1-6}$ alkyl; and A is —$R^6$—CO—X—Y wherein $R^6$ is $C_2$ to $C_6$ branched or linear alkylene;
   X is at least one peptide chain of at least 4 amino acids in length which may be linear, branched or comprise two or more cross-linked polypeptide chains and is selected from insulin, calcitonin, secretin, gastrin, gastrin tetrapeptide, gastrin decapeptide, 34 mer-gastrin, and active fragments thereof; and Y is OH, NH$_2$, or a $C_1$–$C_6$ ester group bonded to the terminal carboxy of the polypeptide chain, and
   ii) orally administering said pharmaceutical composition to a subject in need thereof.

2. The method according to claim 1, wherein the bile salt is mono-, di- or tri-hydroxylated.

3. The method according to claim 1, wherein the bile salt contains a 3α-hydroxyl group.

4. The method according to claim 1, wherein the bile salt is an amphiphilic polyhydric sterol bearing carboxyl groups as part of the primary side chain.

5. The method according to claim 1, wherein the bile salt is underivatised or derivatised.

6. The method according to claim 5, wherein the bile salt is an underivatised bile salt selected from cholate, deoxycholate, chenodeoxycholate and ursodeoxycholate.

7. The method according to claim 6, wherein the bile salt is cholate.

8. The method according to claim 5, wherein the bile salt is a derivatised bile salt selected from taurocholate, taurodeoxycholate, tauroursodeoxycholate, taurochenodeoxycholate, glycocholate, glycodeoxycholate, glycoursodeoxycholate, glycochenodeoxycholate, taurolithocholate and glycolithocholate.

9. The method according to claim 1, wherein the peptide is insulin or an active fragment thereof.

10. An orally administrable pharmaceutical composition, comprising an amide of a bile acid/salt of formula (II):

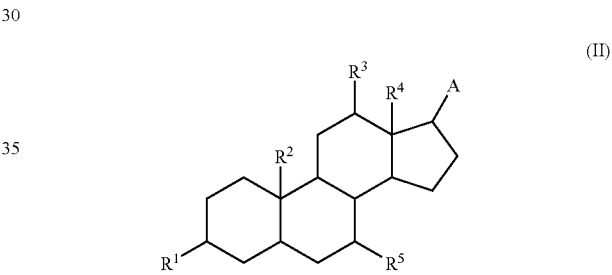

(II)

wherein
   $R^1$ to $R^5$ are independently selected from OH, H or $C_{1-6}$ alkyl; and A is —$R^6$—CO—X—Y, wherein $R^6$ is $C_2$ to $C_6$ branched or linear alkylene;
   X is at least one peptide chain of at least 4 amino acids in length which may be linear, branched or comprise two or more cross-linked polypeptide chains; and
   Y is OH, NH$_2$, or a $C_1$–$C_6$ ester group bonded to the terminal carboxy of the polypeptide chain,
   wherein the pharmaceutical composition is enteric-coated to inhibit degradation in the stomach.

11. The method according to claim 1, wherein the peptide is calcitonin or an active fragment thereof.

12. The method according to claim 1, wherein the peptide is selected from gastrin, gastrin tetrapeptide, gastrin decapeptide, 34 mer-gastrin, and active fragments thereof.

13. The method according to claim 1, wherein the peptide is secretin or an active fragment thereof.

14. A method of treating diabetes mellitus in a subject in need thereof, comprising orally administering to the subject an amide of a bile acid/salt of formula (II):

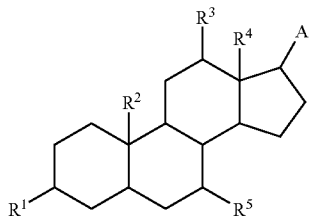

(II)

wherein
R¹ to R⁵ are independently selected from OH, H or $C_{1-6}$ alkyl;
A is —R⁶—CO—X—Y;
R⁶ is $C_2$ to $C_6$ branched or linear alkylene;
X is insulin or an active fragment thereof; and
Y is OH, $NH_2$, or a $C_1$–$C_6$ ester group bonded to the terminal carboxy of insulin or an active fragment thereof.

15. A method of treating osteoporosis in a subject in need thereof, comprising orally administering to the subject an amide of a bile acid/salt of formula (II):

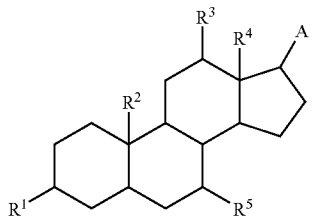

(II)

wherein
R¹ to R⁵ are independently selected from OH, H or $C_1$–$C_6$ alkyl;
A is —R⁶—CO—X—Y;
R⁶ is $C_2$ to $C_6$ branched or linear alkylene;
X is calcitonin or an active fragment thereof; and
Y is OH, $NH_2$, or a $C_1$–$C_6$ ester group bonded to the C-terminus of X.

16. A method of treating a disease associated with a deficiency of secretin in a subject in need thereof, comprising orally administering to the subject an amide of a bile acid/salt of formula (II):

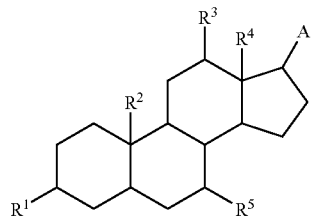

(II)

wherein
R¹ to R⁵ are independently selected from OH, H or $C_{1-6}$ alkyl;
A is —R⁶—CO—X—Y;
R⁶ is $C_2$ to $C_6$ branched or linear alkylene;
X is secretin or an active fragment thereof; and
Y is OH, $NH_2$, or a $C_1$–$C_6$ ester group bonded to the C-terminus of X.

17. A method of treating a disease associated with a deficiency of gastrin in a subject in need thereof, comprising orally administering to the subject an amide of a bile acid/salt of formula (II):

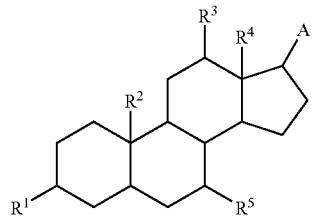

(II)

wherein
R¹ to R⁵ are independently selected from OH, H or $C_1$–$C_6$ alkyl;
A is —R⁶—CO—X—Y;
R⁶ is $C_2$ to $C_6$ branched or linear alkylene;
X is gastrin, gastrin tetrapeptide, 34 mer-gastrin, or an active fragment thereof; and
Y is OH, $NH_2$, or a $C_1$–$C_6$ ester group bonded to the C-terminus of X.

18. A method according to claim 14, wherein the bile acid salt is cholate.

* * * * *